US00PP16851P2

(12) United States Plant Patent
Tellwright

(10) Patent No.: US PP16,851 P2
(45) Date of Patent: Jul. 18, 2006

(54) ***NEMESIA* PLANT NAMED 'FLEURIPI'**

(50) Latin Name: *Nemesia×hybrida*
Varietal Denomination: Fleuripi

(76) Inventor: Martine Tellwright, Highground House, Highground Lane, Barnham, W Sussex (GB), PO22 0BU ( * ) Notice: Subject to any disclaimer, the term of this patent is extended or adjusted under 35 U.S.C. 154(b) by 20 days.

(21) Appl. No.: 11/095,087

(22) Filed: Mar. 30, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Louanne Krawczewicz Myers

(57) ABSTRACT

A new and distinct cultivar of *Nemesia* plant named 'Fleuripi' that is characterized by upright compact habit, medium-green leaves, and flowers that are a strong pink color and which set few seeds. In combination these characteristics set 'Fleuripi' apart from all other existing varieties of *Nemesia* known to the inventor.

1 Drawing Sheet

Genus: *Nemesia.*
Species: ×*hybrida.*
Denomination: Fleuripi.

BACKGROUND OF THE INVENTION

The present invention relates to a new and distinct cultivar of *Nemesia* plant that is grown as an ornamental for border, patio container or hanging basket. The new cultivar is known botanically as *Nemesia×hybrida* and will be referred to hereinafter by the cultivar name 'Fleuripi'. The new variety 'Fleuripi' is floriferous, sets few seeds, exhibits upright compact habit, medium-green leaves, and flowers that are a strong pink color.

'Fleuripi' is a hybrid that resulted from a formal breeding program begun by the inventor in 1998 at her nursery in West Sussex, United Kingdom. The purpose of the breeding program is to produce new varieties of *Nemesia* that exhibit compact habit, new flower color and improved flower size.

In 1999, the inventor cross-pollinated *Nemesia* 'Confetti' (unpatented) as female parent with an unnamed single individual *Nemesia* seedling as male parent. The inventor collected the seed, then sowed and grew to flowering stage many plants from this cross-pollination. From these plants, the inventor selected one plant known to the inventor as *Nemesia* seedling #7 (unpatented), for the purposes of further breeding. In 2000, the inventor deliberately cross-pollinated *Nemesia* 'Confetti' as female parent with and *Nemesia* seedling #7 (unpatented) as male parent. The inventor collected the seed, then sowed and grew to flowering stage many plants from this cross-pollination and from which the inventor selected 'Fleuripi' as a single plant with the desired characteristics described herein.

'Fleuripi' is distinguishable from the male parent *Nemesia* seedling #7 in upright compact growth habit. *Nemesia* seedling #7 exhibits a trailing growth habit. 'Fleuripi' is distinguishable from the female parent 'Confetti' by small size, flower color, and compact growth habit. *Nemesia* 'Confetti' is more than twice the height, with pale pink flowers. The closest comparison plant is *Nemesia* 'Confetti' which exhibits pale pink flowers and tall upright habit.

'Fleuripi' was first asexually propagated by the inventor in 2001 in a cultivated area of West Sussex, United Kingdom using softwood cuttings. The distinguishing characteristics of 'Fleuripi' have been determined stable and are reproduced true to type in successive generations.

SUMMARY OF THE INVENTION

The following traits have been repeatedly observed and represent the distinguishing characteristics of 'Fleuripi'. In combination these traits set the new cultivar apart from all other existing varieties of *Nemesia* known to the inventor. 'Fleuripi' has not been tested under all possible conditions and phenotypic differences may be observed with variations in environmental, climatic, and cultural conditions, however, without any variance in genotype.

1. *Nemesia×hybrida* 'Fleuripi' exhibits upright compact habit.
2. *Nemesia×hybrida* 'Fleuripi' exhibits flowers that are a strong pink color.
3. *Nemesia×hybrida* 'Fleuripi' sets few seeds.
4. *Nemesia×hybrida* 'Fleuripi' is an ornamental that is suitable for use as a border plant, for patio container or hanging basket.
5. *Nemesia×hybrida* 'Fleuripi' is 19 cm. in height and 15 cm. in width at maturity.
6. *Nemesia×hybrida* 'Fleuripi' is floriferous.
7. *Nemesia×hybrida* 'Fleuripi' exhibits medium-green leaves.
8. *Nemesia×hybrida* 'Fleuripi' is hardy to minus 6° Centigrade.

BRIEF DESCRIPTION OF THE DRAWING

The accompanying color drawing illustrates the overall appearance of the new *Nemesia* cultivar 'Fleuripi' showing the colors as true as it is reasonably possible to obtain in colored reproductions of this type. Colors in the drawing may differ from the color values cited in the detailed botanical description, which accurately describe the actual colors of the new variety 'Fleuripi'. The drawing depicts a six months old single plant of 'Fleuripi' which had been grown as follows: a cutting of 'Fleuripi' was rooted in spring in an unheated greenhouse in Bonsall, Calif. in a propagation cell of approximate dimensions 2 cm×2 cm. The resulting young plant was transplanted into a 13 cm diameter round container, pinched once after establishment, and grown without further pinching or chemical growth regulator out of doors until in full flower. The drawing was made using conventional techniques and although colors may appear different from actual colors due to light reflectance, they are as accurate as possible by conventional photography.

BOTANICAL DESCRIPTION OF THE PLANT

Figure 1:
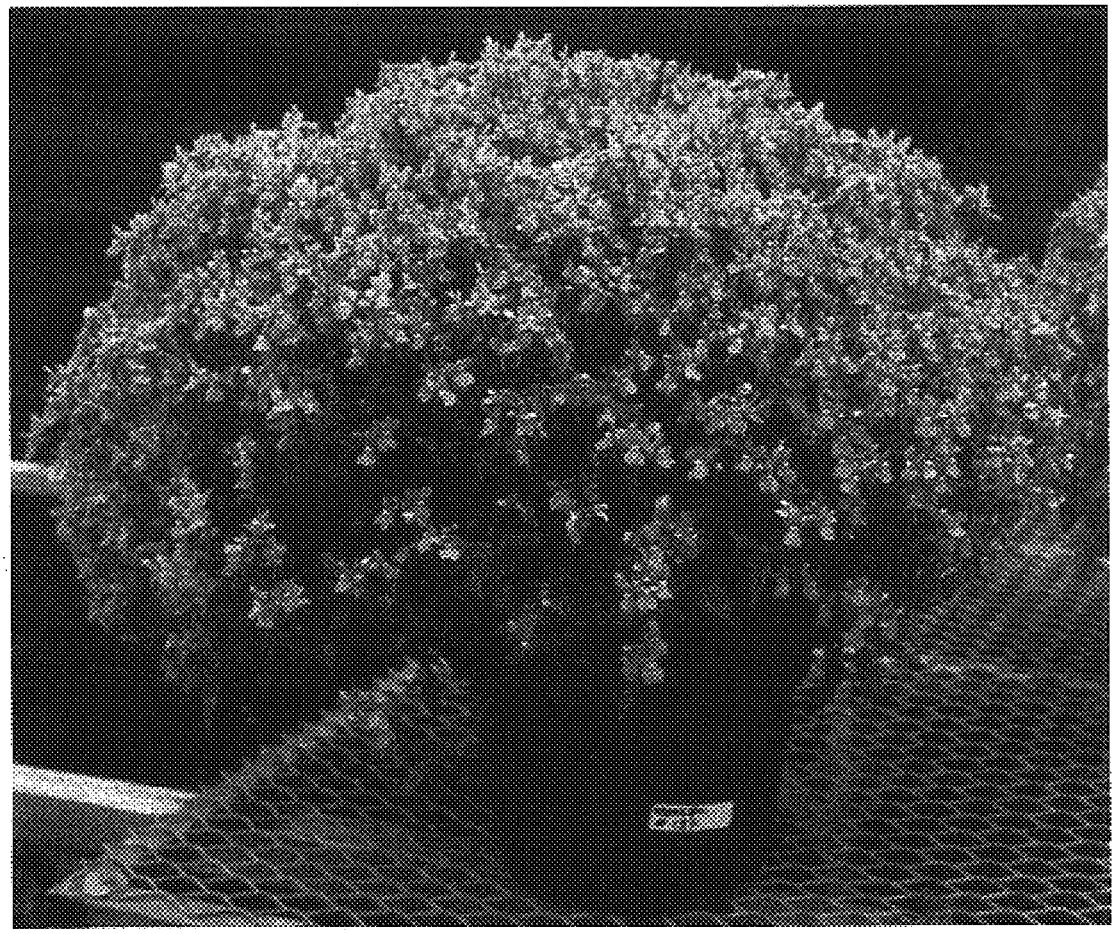

The following is a detailed description 'Fleuripi'. Botanical data was collected in 2004 in Arroyo Grande, Calif. from a two–three months old plant of 'Fleuripi' grown in a 9 cm container in an unheated greenhouse. Phenotypic differences may be observed with variations in environmental, climatic, and cultural conditions. The color determinations are in accordance with the 2001 edition of The Royal Horticultural Society Colour Chart, except where general color terms of ordinary dictionary significance are used.

Botanical classification: *Nemesia×hybrida* 'Fleuripi'.
Genus: *Nemesia.*
Species: *×hybrida.*
Denomination: 'Fleuripi'.
Commercial classification: Ornamental.
Common name: *Nemesia.*
Suggested uses: For border plant, patio container or hanging basket.
Suggested commercial container size: 9 cm.–13 cm diameter.
Cultural needs: Full sun, moist, acidic well-draining soil.
Parentage: *Nemesia* 'Fleuripi' is a hybrid that resulted from the cross-pollination of the following parent plants:
*Seed parent.*—*Nemesia×hybrida* 'Confetti'.
*Pollen parent.*—*Nemesia×hybrida* seedling #7.
Propagation: Softwood cuttings.
Growth habit: Upright, compact habit.
Vigor: Vigorous.
Plant dimensions: Average dimensions of a 9 cm. container plant are 15 cm. in height and 5.50 cm. in width. Dimensions at maturity are 19 cm. in height and 15 cm. in width.
Type: Perennial in USDA zones 9 and warmer; annual in zones colder than zone 9.
Seasonal interest: Flowers that are a strong pink color.
Time to initiate roots: Approximately 14 days are needed to develop roots on initial cuttings.
Temperatures to initiate rooting: The air temperature that is recommended for rooting is 16° Centigrade and the soil temperature that is recommended for rooting is 24° Centigrade.
Crop time: Approximately 8 weeks are needed to produce a finished 9 cm. container plant from a rooted cutting.
Root system: Fine.
Hardiness: Hardy to minus 6° Centigrade.
Disease and pest susceptibility: 'Fleuripi' is susceptible to viruses and whitefly.
Special or recommended growing requirements:
*Pruning.*—Pinch back when potted from plug to commercial container.
*Soil.*—70% medium grade peat, 10% coarse peat and 20% 12 mm. bark.
Growing problems: None known to the inventor.

Stem:
*Stem shape.*—Quadrate.
*Stem length.*—12 cm. in length.
*Stem diameter.*—3 mm. in diameter.
*Stem surface.*—Glabrous.
*Stem color.*—138B.
*Pubescence.*—None observed.
*Stem texture.*—Soft and flexible.
*Internode length.*—3.5 cm. between nodes.
*Branching habit.*—Basal branching.
Foliage:
*Leaf arrangement.*—Opposite.
*Type.*—Evergreen.
*Leaf shape.*—Ovate.
*Leaf division.*—Simple.
*Apex.*—Acute.
*Base.*—Rounded.
*Margins.*—Entire.
*Surface.*—Glabrous.
*Leaf pubescence.*—None observed.
*Leaf appearance* (*abaxial and adaxial surfaces*).—Matte appearance.
*Leaf length.*—Individual leaves range from 1.50 cm. to 3 cm. in length.
*Leaf width.*—Individual leaves range from 4 mm. to 12 mm. in width.
*Leaf color* (*adaxial surface*).—138A.
*Leaf color* (*abaxial surface*).—138B.
*Leaf attachment.*—Petiolate and sessile are present on an individual plant.
*Petiole shape.*—Sulcate.
*Petiole surface.*—Glabrous.
*Petiole dimensions.*—4 mm. in length and less than 1.25 mm. in diameter.
*Petiole color.*—138B.
*Vein pattern.*—Pinnate with mid-vein depressed on adaxial surface and protruding on abaxial surface.
*Vein color* (*adaxial and abaxial surfaces*).—138C.
Flowers:
*Flowering season.*—Spring and summer and fall.
*Fragrance.*—Faintly scented.
*Self-cleaning or persistent.*—Self-cleaning.
*Inflorescence dimensions.*—4 cm. in length and 4 cm. in width.
*Type of inflorescence.*—Terminal racemes.
*Quantity of flowers.*—A range of 8–10 flowers per inflorescence.
*Peduncle dimensions.*—5 cm. in length and 1 mm. in diameter.
*Peduncle shape.*—Quadrate.
*Peduncle surface.*—Glabrous.
*Peduncle color.*—138B.
*Pedicel dimensions.*—9 mm. in length and less than 0.50 mm. in diameter.
*Pedicel shape.*—Closest to cylindrical with one longitudinal furrow.
*Pedicel surface.*—Glabrous.
*Pedicel color.*—138B.
*Bud shape.*—Oval.
*Bud color.*—138A.
*Bud dimensions.*—3 mm. in diameter and 4 mm. in length.
*Quantity of buds.*—A range of 8–10 individual buds are present on an individual inflorescence.
*Flower shape.*—Personate.

*Flower dimensions.*—1.50 cm. in diameter and 1 cm. in depth.
*Flower color.*—77B, 77C and 12A are individually present on an individual flower.
*Corolla tube dimensions.*—9 mm. in length and 2 mm. in diameter.
*Corolla tube color* (*inner and outer surfaces*).—145D.
*Palate color* (*adaxial surface*).—12A.
*Palate color* (*abaxial surface*).—12D.
*Palate dimensions.*—2 mm. in length and 4 mm. in width.
*Nectary color.*—12A.
*Nectary dimensions.*—2 mm. in width and 5 mm. in length.
*Nectary surface.*—Lanate.
*Upper lip dimensions.*—1 cm. in width and 1 cm. in length.
*Upper lip color* (*adaxial surfaces*).—77B.
*Upper lip color* (*abaxial surfaces*).—77C.
*Lower lip dimensions.*—1 cm. in width and 1 cm. in length.
*Lower lip color* (*adaxial surfaces*).—77B.
*Lower lip color* (*abaxial surfaces*).—77C.
*Upper lip margins.*—Entire.
*Lower lip margin.*—Entire.
*Number of lobes* (*upper lip*).—Four lobes in number.
*Fused or unfused* (*upper lip*).—Lobes basally fused.
*Lobe dimensions* (*upper lip*).—Each lobe is 4 mm. in width and 5 mm. in length.
*Upper lip apices.*—Each lobe exhibits a rounded apex.
*Lower lip apex.*—Emarginate.
*Upper lip surfaces* (*adaxial and abaxial*).—Glabrous.
*Lower lip surfaces* (*adaxial and abaxial*).—Glabrous.
*Calyx dimensions.*—3 mm. in length and 4 mm. in width.
*Calyx shape.*—Stellate.
*Sepals.*—Five in number.
*Sepal surface.*—Pubescent.
*Sepal apex.*—Acute.
*Sepal shape.*—Lanceolate.
*Sepal dimensions.*—2 mm. in length and 1 mm. in width.
*Sepal margin.*—Entire.
*Sepals fused or unfused.*—Basally fused.
*Sepal color* (*adaxial surface*).—138A.
*Sepal color* (*abaxial surface*).—138A.
*Lastingness of individual flower on the plant.*—An individual flower lasts 7–10 days.

Reproductive organs:
*Stamens.*—Four in number.
*Color of stamens.*—155A.
*Stamen dimensions.*—1 mm. in length and less than 0.25 mm. in diameter.
*Anther color.*—163C.
*Amount of pollen.*—Moderate.
*Pollen color.*—163C.
*Anther dimensions.*—Less than 0.50 mm. in length and less than 0.50 mm. in width.
*Pistil.*—One.
*Pistil color.*—144D.
*Pistil dimensions.*—1 mm. in length and 0.25 mm. in diameter.
*Ovary dimensions.*—0.50 mm. in height and 0.50 mm. in diameter.
*Ovary shape.*—Globular.
*Ovary position.*—Superior.
*Ovary color.*—144D.

Seed:
*Quantity of seed.*—'Fleuripi' sets few seeds, an average of 2 per flower.
*Seed shape.*—Flattened oval.
*Seed color.*—200D.
*Seed dimensions.*—An average of 2 mm. in length and 1.25 mm. in width.

What is claimed is:

1. A new and distinct cultivar of *Nemesia* plant named 'Fleuripi' as described and illustrated herein.

* * * * *